United States Patent [19]

Feinbloom

[11] 4,364,645
[45] Dec. 21, 1982

[54] ADJUSTABLE FRAME APPARATUS FOR TELESCOPIC SPECTACLES

[76] Inventor: William Feinbloom, P.O. Box 411, New Paltz, N.Y. 12561

[21] Appl. No.: 211,468

[22] Filed: Nov. 28, 1980

[51] Int. Cl.³ .......................... G02C 5/14; A61B 3/10; G03B 1/58
[52] U.S. Cl. .................................. 351/204; 351/158; 351/120
[58] Field of Search ................. 351/5, 41, 55, 57, 158, 351/120; 33/200

[56] References Cited
U.S. PATENT DOCUMENTS
2,273,456 9/1966 Feinbloom ........................ 351/158

Primary Examiner—John K. Corbin
Assistant Examiner—Rodney B. Bovernick
Attorney, Agent, or Firm—Arthur L. Plevy

[57] ABSTRACT

There is disclosed a trial frame employed for determining interpupillary distances and the angle of inclination for persons having low or reduced vision. The frame has inserted therein test carrier lenses for each eye. The carrier lenses possess an arcuate aperture for pivotally adjusting a telescopic lens assembly which is moved within the aperture to determine the correct interpupillary distance for each eye. The temple of the frame is secured to the front of the frame by a pivot member which enables the practitioner to pivot or incline each temple with respect to the front to obtain an optimum angle of inclination to thereby enable the practitioner to prepare a final spectacle assembly employing a prescribed carrier lens together with optimum telescope assemblies strictly according to the requirements of the individual patient.

10 Claims, 4 Drawing Figures

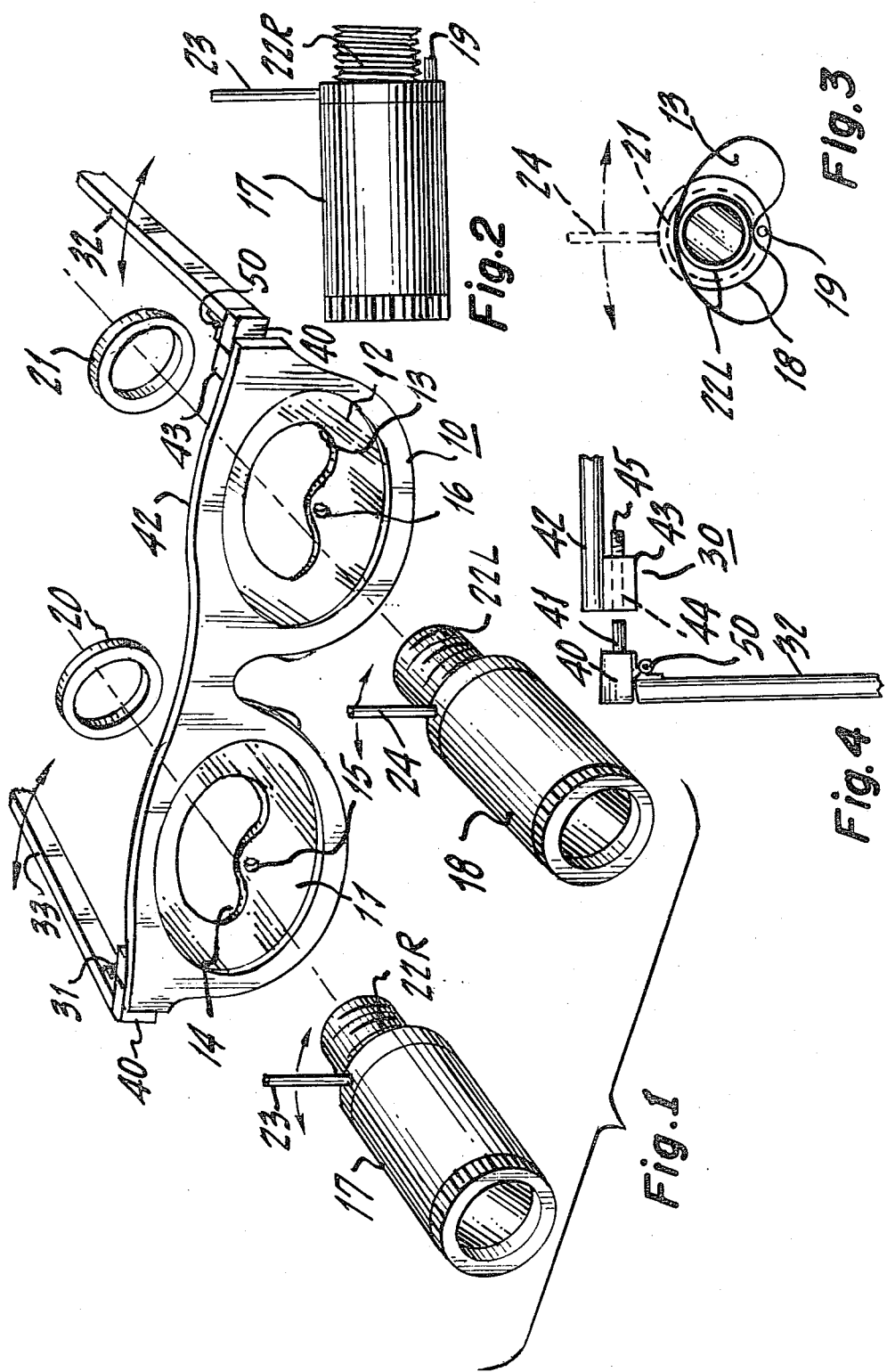

ADJUSTABLE FRAME APPARATUS FOR TELESCOPIC SPECTACLES

BACKGROUND OF THE INVENTION

This invention relates to telescopic spectacles in general and more particularly to a trial frame for enabling a practitioner to specify a proper frame and prescription to a person having reduced vision.

Telescopic spectacles are widely employed to assist persons who have severe vision handicaps. Essentially, such persons are designated as low vision individuals where, due to deterioration, their vision is reduced by factors of up to ninety percent or more. There are many conditions which will provide such optical atrophy, such as retinal degeneration, partial cataracts and other severe problems. Essentially, the reduction of vision requires such individuals to use spectacles which possess a prescribed carrier lens to enable them to maintain a complete field of vision for use in negotiating in close quarters such as walking up or down steps and for short distance vision and so on.

In regard to such individuals, the carrier lens or spectacles also have coupled thereto a telescopic lens assembly to afford vision at a reduced field of view which will enable such persons to see at longer distances necessary for operating a vehicle, reading, working and so on. Telescopic spectacles are magnifying systems used by persons having such reduced vision.

As indicated, low vision patients have a decreased central vision. Such patients use an area of the retina other than the center or the macula to enable them to utilize their best vision capabilities. Hence, in such individuals, their line of sight which is the line joining the best area of their retina drawn to the point of fixation, is at a different lateral position than the normal line of sight. In order for a practitioner to fit or adjust such an individual with proper telescopic spectacles, the practitioner must be able to accurately measure the line of sight for each patient.

Regular trial frames which are used in normal refraction techniques are not adequate to accommodate low vision patients who require telescopic spectacles. In order to obtain an appropriate fitting in a low vision examination, it is necessary to align the axis of the telescope with the line of fixation of the eye under examination. In order to do so, the practitioner must obtain the exact interpupillary distance between the patient's eyes. In a low vision case, the interpupillary distance of each optic axis of the telescope from the center of the noise piece must be independently located by the practitioner. Apart from this important consideration is that the final spectacle frame to be prescribed for the patient must rest on the nose and ears of the patient in a predetermined orientation. This depends on the width of the bridge, the size of the eye, the length of the temple and the inclination between the temple and the front plane of the spectacle.

In order to properly prescribe a final pair of spectacles for the patient, the practitioner must adjust the patient's vision according to the precise frame or a substantial duplicate of the precise frame that the patient is going to use. For example, typical frame sizes which can accommodate telescopic lenses are available in 44, 46, 48 mm eye sizes and 20, 22, 24 mm bridge sizes with temple lengths of $5\frac{1}{2}$, $5\frac{3}{4}$ and 6" in length.

It is an object of the present invention to provide a trial frame which a practitioner can use to specify the optimum position for a telescopic lens assembly employed in spectacles. It is a further object of this invention to provide a trial frame assembly which enables the practitioner to obtain the exact interpupillary distance and to further enable the practitioner to accurately specify the angle of inclination of the telescope about a horizontal axis to thereby enable the patient to achieve the optimum use of the telescope assembly together with correction lenses.

BRIEF DESCRIPTION OF THE PREFERRED EMBODIMENT

A trial frame for enabling prescribed measurements for spectacles used to compensate for vision defects in a handicapped user, comprising a spectacle frame having at least one test carrier lens emplaced in the eyepiece of said frame, said lens including an elongated aperture of a length selected to provide a given range manifesting average interpupillary distances associated with a user, and a telescopic assembly positioned in said aperture to enable a practitioner to move said assembly within said aperture when said frame is accommodated on the face of said user to determine said interpupillary distance of said user.

BRIEF DESCRIPTION OF THE FIGURES

FIG. 1 is a perspective plan view depicting a trial frame spectacle arrangement according to this invention;

FIG. 2 is a side elevational view of a telescope assembly employed in this invention;

FIG. 3 is a front view depicting the adjustment afforded to measure interpupillary distance; and FIG. 4 is a partial diagrammatic view depicting an inclination adjustment accommodated by the trial frame.

DETAILED DESCRIPTION OF THE INVENTION

Referring to FIG. 1, there is shown a trial frame 10 according to this invention. As indicated, the practitioner will have a trial frame as 10 for each frame type the patient may select. Once the patient selects a desired frame, the trial frame as 10 is emplaced upon the face of the person as is conventional.

As can be seen from FIG. 1 in the eye wire of the frame 10, there is positioned a set of plano plastic carrier lenses 11 and 12. Into each lens, there is cut an arcuate aperture as 13 and 14. Beneath the center line of the arcuate apertures 13 and 14 are two small holes 15 and 16 which are used to accommodate a pin associated with the telescope assembly to enable pivoting of the assembly within the arcuate aperture.

As shown in FIG. 1, two telescopic assemblies 17 and 18 are emplaced within the arcuate apertures 13 and 14. Each telescopic assembly as depicted in FIG. 2 has a pin 19 which is pivotally inserted into apertures 15 and 16. The telescopic assemblies are held within the apertures by means of nylon retaining nuts or washers 20 and 21 which threadily engage the front portion 22 of the telescope assembly.

Secured to the body portion of the telescopic assemblies 17 and 18 are extending adjustment rods 23 and 24 which enable the practitioner to move or pivot the telescopic assemblies 17 and 18 within the arcuate apertures 13 and 14. This provides movement to enable the practitioner to vary the interpupillary distances between desired limits. In a typical case, this would be between 48 mm to 78 mm and he does so by accessing rods 23 and 24.

As the adjustments are made, the patient reports to the practitioner his view of a chart which he is viewing during adjustment of the telescope assemblies. When the patient reports a complete circular field in space, the correct interpupillary distance is achieved. At this position, the practitioner then firmly locks the associated nuts 20 and 21 to maintain the telescope assembly in a desired position.

Telescope assemblies as 17 and 18 are well known in the optical field and are generally of the appearance as shown in FIG. 1 with the exception that they are not normally associated with rods 23 and 24. In any event, such assemblies as 17 and 18 are available in magnifications of $3\times$, $4\times$, $5\times$, $6\times$, $7\times$, $8\times$ and so on and are interchangeable for examination in the same frame. It is, of course, ascertained that the practitioner can replace one telescope assembly with another by merely removing the nylon nuts 20 and 21.

When the telescopes are properly adjusted to achieve optimum interpupillary distances, another problem exists. When the frame 10 is properly placed on the patient's face, his line of sight may pass through the carrier lens portion at a distance higher than the geometric center of the lens. This distance may be about 3 to 6 mm or on an average, about 4 mm. For purposes of explanation, it is assumed that the line of sight through this point is now parallel to the ground and it is thus specified that the patient's head and eye are in the primary position. However, in order for the patient to wear telescopic spectacles in a bioptic position, the axis of the system is placed above his line of sight so that the mounting of the telescopes will not block his vision when he is using the carrier lens or when he walks or drives. Accordingly, the optic axis of the telescope must be located above or higher than the 4 mm point where his line of sight intersected the carrier and the angle of inclination of the axis of the telescope must also be changed. This is so because as the patient makes a compensatory movement by lowering his head downward (chin goes down and in), he must also roll or rotate his eye upward at an angle to compensate the downward rotation of his head. When he rotates his head downward, he also moves the spectacles and hence, the telescopes. This motion is conventionally employed by such patients to enable them to view through the carrier lens when desired. To compensate for this downward rotation, there are rotatable or pivotable inclination assemblies 30 and 31 secured between each temple 32 and 33 and the front of the frame. The rotating or pivoting inclination assemblies enable the practitioner or patient to turn the front portion of the frame or that portion holding the carrier lens and telescopes in an outward or upward direction as depicted by the arrow on FIG. 1 to compensate for the head motion. The frame is thus adjusted by the practitioner until the patient sees a proper alignment when viewing the chart. In this manner, the frame is tilted or inclined until the patient exhibits accurate vision within the center of his particular field. When this is accomplished, the practitioner employs a protractor to read the angle between the plane of the carrier lens and the plane of the temple. An angle of 10° is deducted from the value read as this angle is the natural inclination of the carrier with respect to the temples when the frame is first manufactured. Thus, the reading of the protractor minus 10° is the angle at which the final carrier lens must be drilled to set the telescope properly at the position equivalent to the exact interpupillary distance. The practitioner, while adjusting the trial frame 10 for both interpupillary distance and inclination, should observe the real illuminated exit pupil of the telescope that illuminates the patient's cornea while the patient fixates the distant test chart. This is done as the exit pupil is formed at different distances behind the last glass surface of the telescope depending upon the magnification of the particular telescope. For example, for a $6\times$ telescope, the distance is 9.7 mm behind the last surface.

It is, of course, also possible to vertically adjust the telescope from 0 to 8 mm above the geometric center of the lens. However, based on observation, it has been determined that once the proper inclination and interpupillary distances are obtained, the vertical displacement does not seem to matter to the patient.

FIG. 3 depicts in schematic diagram form the movement of the telescope assembly within an arcuate aperture as 13 to achieve interpupillary distances.

FIG. 4 shows a simple schematic diagram of the inclination assembly positioned between each temple piece and the front of the frame. Essentially, the assembly for obtaining inclination at the temples consists of a first member 40 having a cylindrical projection 41 which is carried by the temple member. The front of the frame 42 has secured thereto an apertured member 43. Member 43 has an aperture 44 for accommodating the cylindrical projection 41 and is associated with a set screw 45 which coacts with the aperture. Thus, the cylindrical projection 41 rotates within the aperture 44 in a friction fitting. The set screw is employed to adjust the force required to provide inclination. Thus, the front of the frame can be tilted with respect to the temples in a completely continuous manner. The practitioner, by bending the temples while the spectacle is emplaced on the patient's face, can therefore provide any desired inclination. There are, of course, other mechanisms for accomplishing such adjustment.

Also shown is a conventional hinge assembly 50 which is secured to the temple member 32 to enable one to fold the temples with respect to the frame as in a conventional pair of spectacles to thus accommodate storage when not in use.

As indicated above, the telescopes as 17 and 18 are held in place relatively perpendicular to the carrier lens by the nylon nuts 20 or 21. The eyepiece end of the telescope as depicted in FIG. 2 is threaded to enable engagement of the nylon nut to thereby enable the practitioner to move or lock the telescope to the carrier lens. Initially, the two telescopes are aligned on a collimator to assure that they are parallel and once aligned, they maintain parallelism throughout the adjustment range afforded by the arcuate apertures. The parallelism for inclination is easily obtained by inclining whichever side needs to be further inclined.

In view of the fact that patients may require sphero correction lens from $+20$ D.S. to $-20$ D.S. (D.S. equals diopter sphere), such correction lens are made in caps that fit over the eyepieces.

Essentially, the trial frame when adjusted as described above now enables the practitioner to prepare the spectacles strictly according to the needs of the patient. Thus, the practitioner now knows exactly the patient's correct interpupillary distance and can now drill holes in correct carrier lenses to permanently accommodate the final telescope assemblies. These holes are drilled at the angle determined by the inclination measurement performed above and hence, the patient will then have a final pair of spectacles which include the exact frame selected with both the carrier and telescope assemblies being perfectly aligned to compensate for his particular visual problems.

It is thus seen that the above described trial frame enables a practitioner to quickly and accurately obtain interpupillary distance measurements and proper inclination for low vision patients. The structure enables the measurements to be done accurately and rapidly, thus affording a considerable savings of time and effort in regard to the practitioner and the patient.

It is understood that many alternative embodiments may be discerned by those skilled in the art, all of which are deemed to be encompassed by the claims appended hereto.

I claim:

1. A trial frame for enabling prescribed measurements for spectacles used to compensate for vision defects in a handicapped user, comprising:
   (a) a spectacle frame having at least one test carrier lens emplaced in the eyepiece of said frame, said lens including an elongated aperture of a length selected to provide a given range manifesting average interpupillary distances associated with a user, and
   (b) a telescopic assembly positioned in said aperture to enable a practitioner to move said assembly within said aperture when said frame is accommodated on the face of said user to determine said interpupillary distance of said user.

2. The trial frame according to claim 1 further including:
   (a) inclination means coupling at least one temple piece of said frame to the front of said frame carrying said lenses to enable tilting of said front with respect to said temple.

3. The trial frame according to claim 1 wherein said aperture is an arcuate aperture.

4. The trial frame according to claim 1 wherein said test carrier lens is fabricated from plastic.

5. The trial frame according to claim 3 wherein said test carrier lens has a smaller aperture centrally located with respect to said elongated aperture and pivot means coupled to said telescopic assembly for coacting with said smaller aperture to enable a pivotal movement of said telescopic assembly within said elongated aperture.

6. The trial frame according to claim 2 wherein said inclination means includes a first member secured to said temple and having an extending projection rod, a second member having an aperture for accommodating said rod, said second member secured to the front of said frame near said temple to enable the selective inclination of said frame front with respect to said temple.

7. The trial frame according to claim 1 further including locking means coupled to said telescope and adapted when actuated to lock said telescopic assembly within said aperture at a desired position.

8. The trial frame according to claim 1 further including adjusting means coupled to said telescopic assembly to aid in moving said assembly when emplaced in said elongated aperture.

9. A method of measuring the interpupillary distance and angle of inclination of a low vision person, comprising the steps of:
   (a) emplacing a trial frame on the face of said person,
   (b) moving a telescopic assembly along a predetermined path within the eyepiece of said frame while the person fixates on a vision chart,
   (c) ceasing movement of said assembly when the person indicates a full field of view via said assembly,
   (d) tilting said frame with respect to the temple pieces according to a movement of said patient's head necessary to compensate for full field vision.

10. The method according to claim 9 further including the step of:
    (a) measuring said angle of tilt of said frame with respect to said eyepiece for determining a final angle for permanently mounting a telescopic assembly in a final frame.

* * * * *